Figure 1:
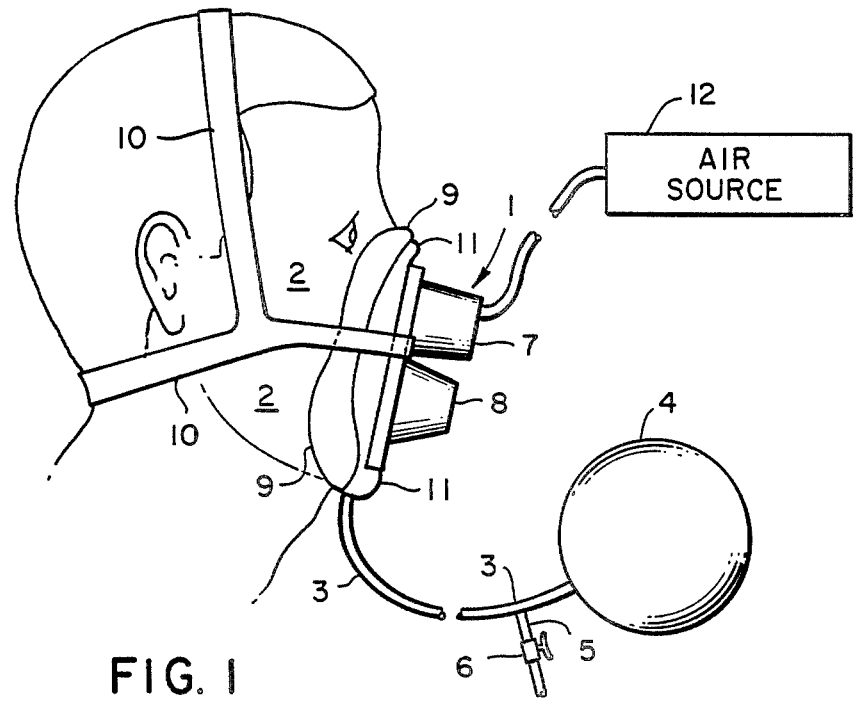

United States Patent [19]

Toffolon

[11] Patent Number: 4,971,051
[45] Date of Patent: Nov. 20, 1990

[54] PNEUMATIC CUSHION AND SEAL

[76] Inventor: Norman R. Toffolon, P.O. Box 356, Harrington, Me. 04643

[21] Appl. No.: 318,494

[22] Filed: Mar. 2, 1989

Related U.S. Application Data

[63] Continuation of Ser. No. 73,164, Jul. 13, 1987, abandoned.

[51] Int. Cl.$^5$ ............................................. A62B 18/08
[52] U.S. Cl. ........................... 128/206.26; 128/206.28
[58] Field of Search ......... 128/205.28, 206.21–206.24, 128/206.26, 207.13, 201.23–201.25

[56] References Cited

U.S. PATENT DOCUMENTS

| 1,108,122 | 7/1914 | Drager | 128/206.26 |
| 2,254,854 | 9/1941 | O'Connell | 128/206.26 |
| 3,044,464 | 7/1962 | Gray | 128/206.26 |
| 4,305,387 | 12/1981 | Kundig et al. | 128/206.26 |
| 4,402,316 | 9/1983 | Gadberry | 128/206.24 |
| 4,677,977 | 7/1987 | Wilcox | 128/206.24 |

FOREIGN PATENT DOCUMENTS

| 801629 | 5/1936 | France | 128/201.23 |
| 858749 | 5/1940 | France | 128/201.23 |
| 326983 | 6/1935 | Italy | 128/206.26 |
| 775911 | 5/1957 | United Kingdom | 128/206.26 |

*Primary Examiner*—Randall L. Green
*Assistant Examiner*—K. M. Reichle
*Attorney, Agent, or Firm*—Daniel H. Kane

[57] ABSTRACT

A face mask having a perimeter for sealing against the face of a user is incorporated in a continuous positive airway pressure mask (CPAP) for treatment of central and obstructive sleep disorders. An elongate flexible pneumatic cushion seal is formed around the perimeter of the mask. An air passageway is coupled to the pneumatic air cushion. An inflatable expandable balloon chamber is coupled in open communication through the air passageway to the elongate pneumatic cushion seal. The balloon chamber is inflated to a desired pressure for passage of air between the pneumatic cushion seal and the expandable balloon chamber at said pressure. The pneumatic cushion seal is maintained against the face of a user and follows the changing contours of a user's face by passage of air between the pneumatic cushion seal and the expandable balloon chamber at the desired pressure. This changing volume of air in the pneumatic cushion seal assures that the seal is maintained. A flap ring of a flexible membrane positioned at the perimeter of the mask extends radially inwardly from the perimeter. The flexible membrane flap ring is formed with a central opening for the user to breathe in the mask. Air flowing into the mask seals the flexible membrane flap ring against the facial contours providing additional sealing for the CPAP mask.

8 Claims, 1 Drawing Sheet

PNEUMATIC CUSHION AND SEAL

This application is a continuation, of application Ser. No. 073,164, filed 7/13/87, now abandoned.

FIELD OF INVENTION

This invention relates to a pneumatic cushion with sealing device which is incorporated in a Continuous Positive Airway Passage Mask (CPAP) used for the treatment of central and obstructive sleep disorders.

DISCUSSION OF PRIOR ART

Central and obstructive sleep disorders may be caused by a narrowing or obstruction in the throat of the sufferer during sleep. This narrowing or obstruction closes the air passage of the nose and throat anywhere from ten to seventy times per hour; during these periods, a sufferer will partially awake and will be unable to breathe for lengths up to ten seconds in duration. The sufferer does not realize that his breathing has been interrupted, however the interruptions keep him from falling into deep sleep, which one requires to function normally. In summary, a sufferer will never get a good night's sleep and he will not know it.

Currently, central and obstructive sleep disorders are treated by application of a CPAP system, where air pressure is applied through a face mask, keeping the air passage open in the nose and mouth. CPAP treatment is a successful non-surgical treatment for both central and obstructive disorders.

OBJECTS

Accordingly several objects of my invention are:

That it creates an air seal between the mask and the user's face and ensures that the continuous pressure necessary to keep the air passage open is maintained.

That by utilizing my invention, less air pressure is necessary to keep the air passage open than is required with the current technology.

That my invention alleviates the need for a tight fit between the CPAP mask and the user's face; thus avoiding skin irritations and abrasions.

That my invention makes the CPAP mask self-adjusting so that a user's movements during sleep do not break the seal between mask and face.

That the user can adjust the pressure to his personal comfort level without losing the seal between mask and face; and further that adjustments to compensate for differences and changes in atmospheric pressure can be made without affecting the seal.

Further objects and advantages of my invention will become apparent from a consideration of the drawings and ensuing description thereof.

DRAWINGS

FIG. 1 Side view of a standard CPAP mask with pneumatic cushion and seal showing, as applied against the face of a user.

Figure 2:
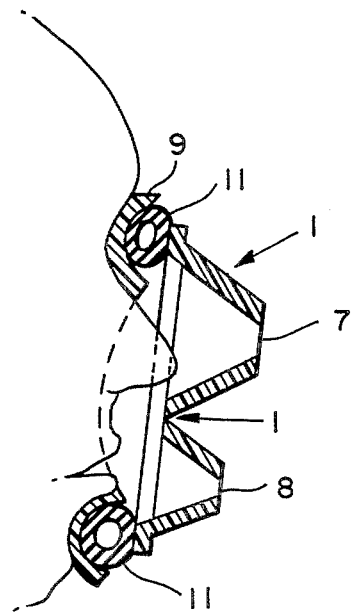

FIG. 2 A vertical sectional view through the CPAP mask shown in FIG. 1.

DESCRIPTION

The standard mask (1) contains an inlet (7) and an outlet (8) for air. Attached to the standard mask (1) is a pneumatic cushion (11), methods of attachment include but are not limited to mechanical fastening or adhesives.

A passageway (3) for air (including but not limited to a hose) is attached to the pneumatic cushion (11).

At the other end of the air passageway (3) is a balloon (4) or similar device capable of expanding and maintaining designated air pressures. Also attached to the air passageway (3) is a hose (5) containing a valve (6). This allows for an increased or decreased volume of air by flow of air in or out of the closed system (11,2,3,4,5).

Attached to the pneumatic cushion (11) and surrounding the perimeter of the pneumatic cushion is a piece of plastic or other flexible material called the "flap ring" (9) which is applied against the user's face (2). Continuous air pressure from the air flow within the standard mask, (1), pushes against the flap ring, (9), and creates a seal between the user's face (2) and the flap ring (9). Said flap ring (9) can be attached directly to the standard mask (1) if the pneumatic cushion (11), is not used. Said attachment may be achieved by means including but not limited to mechanical fastening or the application of adhesives.

OPERATION

The object of creating a seal between the standard CPAP mask (1), and the user's face (2) may be accomplished in three ways:
 (a) By means of the flexible pneumatic cushion (11) held in place by the harness (10).
 (b) By means of the flap ring (9) held in place by continuous air pressure from flow of air entering from inlet (7).
 (c) By combining means (a) and (b) above.

(a) The Flexible Pneumatic Cushion

A hollow cushion is shaped and sized to fit various CPAP masks (1). The CPAP mask (1) is held in position on the user's head via a set of straps (10). Connected to the pneumatic cushion (11) is a balloon or similar device (4), which is kept well away from the user by means of an air passageway or hose (3). The user admits air to the balloon (4) through a hose, (5) and a valve (6), which increases or decreases the air pressure within the balloon (4). The air pressure within the balloon (4) in turn determines the air pressure within the pneumatic cushion (11) as air passes into the cushion via an air passageway or hose (3). The user introduces air into the valve (6), the balloon (4) inflates to an initial starting volume and transfers pressure to the pneumatic cushion (11) via the air passageway or hose (3). The user can decrease the pressure within the pneumatic cushion (11) by opening the valve (6), thus releasing air from the balloon or similar device (4).

The user can thus introduce an amount of air into the system which will create a seal as the pressure molds the material of the pneumatic cushion (11) to the contours of the user's face (2). Since each user controls the amount of pressure within his system, adjustments can be made to ensure maximum comfort on an individual basis. Both the integrity of the seal and the comfort level are assured even as the contours of the user's face change during the sleep period since air is transferred back and forth between the pneumatic cushion (11) and the balloon (4) via the air passageway (3) thereby expanding the balloon from the starting volume and contracting the balloon. The volume of air within the air cushion may change as facial expressions shift, however the flexible material of the cushion (11) continues to seal comfortably against the user's face (2).

(b) The Flap Ring

A flap ring (9), with or without the pneumatic cushion (11), can also be used to create a seal between the CPAP mask (1) and the user's face (2). The flap ring (9) is a flexible membrane which surrounds the perimeter of the mask (1) and is affixed to the mask. The flap ring (9) has an opening large enough to permit the user's nose and mouth to enter the mask (1) in the case of a full face mask, or just the user's nose in the case of a nasal face mask.

The continuous air pressure and the air flow from a source of air 12 introduced into the mask at inlet (7) as treatment for central and obstructive sleep disorders (and other conditions treated with a CPAP mask) pushes the extended side surface area of the flap ring (9) membrane against the user's face (2) as shown in FIG. 2, thus creating the desired seal between mask and face. Because the flap ring (9) membrane is flexible, it permits changes in facial contours to occur without loss of the seal.

(c) Combining Means (a) and (b) Above

The pneumatic cushion (11) and flap ring (9) (the operation of each having been described above) can be used together to form the desired air seal. Depending on the design of the underlying CPAP mask (1), means (a), (b) or (c) may result in the optimal seal.

While the descriptions found in the "Operation" section contain many specificities, these should not be construed as limitations on the scope of the invention, but rather as an exemplification of one preferred embodiment thereof. Many other variations are possible, for example the use of this invention to seal devices other than masks or to create a cushioning effect through use of the pneumatic system. Accordingly, the scope of the invention should be determined not only by the embodiment illustrated, but also by the appended claims and their legal equivalents.

I claim:

1. A breathing apparatus comprising:
   a face mask having a perimeter for fitting against the face of a user, said face mask having a breathing air inlet for flow of air into the mask and an air outlet for flow of air out of the mask;
   an elongate flexible pneumatic cushion seal formed around the perimeter of the mask for flexibly engaging the face of a user and forming a seal to prevent flow of air between the perimeter of the mask and face of the user;
   means for mechanically securing the face mask on a user with the pneumatic cushion seal held against the face of the user to form said seal;
   an air passageway coupled to the pneumatic cushion seal;
   inflatable, expandable and contractible balloon chamber means coupled to said air passageway and in open communication through the air passageway to the elongate pneumatic cushion seal, said balloon chamber means being inflatable to an initial starting volume to provide a desired pressure, said air passageway permitting passage of air back and forth between the pneumatic cushion seal and the expandable and contractible balloon chamber means substantially at said pressure;
   said balloon chamber means being expandable from said initial starting volume to an expanded volume greater than the starting volume when receiving air from the flexible pneumatic cushion seal, and being contractible when air flows therefrom into the flexible pneumatic cushion seal;
   whereby the pneumatic cushion seal can be maintained against the face of a user and follow the changing face contours during user movement by passage of air between the pneumatic cushion seal and expandable and contractible balloon chamber means substantially at the desired pressure thereby changing the volume of air in the pneumatic cushion seal in response to user movement.

2. The apparatus of claim 1 further comprising a second air passageway, branch coupling means operatively coupling said second air passageway into the first air passageway at a location between the pneumatic cushion seal and balloon chamber means, and valve means located in the second air passageway for controlling inflation of said balloon chamber means from a pressurized source of air to the desired pressure and for controlling release of air from the pneumatic cushion seal and balloon chamber means for adjusting the volume and pressure of air in the pneumatic cushion seal and balloon chamber means.

3. The apparatus of claim 1 further comprising a source of pressurized breathing air coupled to the face mask breathing air inlet whereby the face mask comprises a continuous positive airway pressure mask.

4. The apparatus of claim 1 further comprising:
   a flap ring secured to the face mask and formed around the perimeter of the mask comprising a flexible, flappable membrane extending radially inwardly from the pneumatic cushion seal on the side of the pneumatic cushion seal which is adapted to be adjacent to and engage the face of a user, said flap ring having a central opening for user breathing into the mask and an extended side surface area adapted to lie loosely in front of the face of a user around the inside of the perimeter of the mask in the absence of air flow, said flexible membrane being, constructed, arranged and oriented so that a flow of air into the mask pushes the extended side surface area of the flap ring to lie flat on and follow the face contours of a user for increasing the seal of the perimeter of the mask on the face of a user by developing a seal between the extended side surface area of the flap ring and the face of the user.

5. The apparatus of claim 4 wherein the flap ring is adhesively bonded to the pneumatic cushion seal and extends over the side of the pneumatic cushion seal adapted to engage a user's face.

6. A breathing apparatus comprising:
   a breathing face mask having a perimeter with bearing means for fitting against the face of a user, said face mask having a breathing air inlet for flow of air into the mask and an air outlet for flow of air out of the mask;
   means for mechanically securing the face mask on a user with the bearing means held against the face of the user; and
   a flap ring secured to the face mask and formed around the perimeter of the mask comprising flappable flexible membrane means extending radially inwardly from the perimeter of the mask, said flexible membrane means for lying loosely in front of the face of the user radially inward of the perimeter of the mask in the absence of air flow notwithstanding pulling of the mask against the face of the user by the mechanically securing means, said flexible membrane means also for being pushed in the presence of air flow to lie flat on the facial contours of the user thereby developing a seal around the perimeter of the mask between the the flap ring and face of the user;

said flexible membrane means including central opening means for allowing fluid communication between the mask interior and the user and extended surface means to contact the facial contours of the user.

7. The apparatus of claim 6 further comprising an elongate flexible pneumatic cushion seal means formed around the perimeter of the mask for flexibly engaging the face of the user and forming a seal to prevent flow of air between the perimeter of the mask and face of the user, said flap ring being joined to the face mask over the side of the pneumatic cushion seal means adapted to lie on the face of the user.

8. The apparatus of claim 7 further comprising:
an air passageway means coupled to the pneumatic cushion seal means;
and an inflatable expandable and contractible balloon chamber means coupled to said air passageway means and in open communication through the air passageway means to the pneumatic cushion seal means for passage of air through said air passageway means back and forth between the pneumatic cushion seal means and expandable and contractible balloon chamber means in response to user movement.

* * * * *